United States Patent [19]
Clark

[11] Patent Number: 5,623,251
[45] Date of Patent: Apr. 22, 1997

[54] DEVICE TO VERIFY THE IDENTITY OF A FLUID FOR PROPER SELECTION OF STORAGE VESSEL

[76] Inventor: John H. Clark, P.O. Box 1144, Ponchatoula, La. 70454

[21] Appl. No.: 438,505

[22] Filed: May 10, 1995

[51] Int. Cl.⁶ .................................................. G08B 21/00
[52] U.S. Cl. .................. 340/603; 340/618; 340/623; 340/624; 340/625; 73/440; 73/451
[58] Field of Search ................................. 340/603, 618, 340/623, 624, 625; 73/290 R, 305, 306, 307, 309, 311, 440, 451; 417/1, 40, 63

[56] References Cited

U.S. PATENT DOCUMENTS

| 3,946,625 | 3/1976 | Miyazaki et al. | 340/623 |
| 4,629,398 | 12/1986 | Cahalan | 340/623 |

Primary Examiner—Thomas Mullen
Assistant Examiner—Julie B. Lieu
Attorney, Agent, or Firm—Joseph N. Breaux

[57] ABSTRACT

Disclosed is a device used to verify the identity of a selected fluid before permitting the selected fluid to be introduced into a storage vessel containing a liquid of known specific gravity. The device includes a container constructed from connecting walls to form a chamber having an opening through which a selected fluid may be introduced; a first float switch positioned in the container for generating a first signal when contacted by a fluid having a specific gravity greater than a first predetermined amount; a second float switch positioned in the container for generating a second signal in the presence of a fluid having a specific gravity greater than a second predetermined amount, where the first predetermined amount is less than the second predetermined amount, and the second float switch is responsive to the first signal from the first float switch.

10 Claims, 3 Drawing Sheets

DEVICE TO VERIFY THE IDENTITY OF A FLUID FOR PROPER SELECTION OF STORAGE VESSEL

FIELD OF INVENTION

This invention relates to devices for distinguishing between fluids based upon specific gravity, and in particular, to distinguish between jet fuel and AVGAS prior to transferring liquid into a storage tank.

BACKGROUND ART

In aviation, two types of fuel are generally used, jet fuel (kerosene) and AVGAS. Placement of jet fuel in an aircraft engine designed to operate on AVGAS, or vice versa, can cause damage to the engine with potentially catastrophic results to the aircraft and passengers. Accordingly, it is important that the two fuels do not become confused with one another, or mixed with one another. For this reason, the two fuel types are stored onsite at an airport in separate tanks. Furthermore, tankcars for transporting aviation fuels are dedicated to such fuels. It is usual practice for a tankcar operator to dedicate a transportation tankcar for use with only AVGAS or jetfuel. However, such dedication is not required, and consequently, confusion can arise as to the type of fuel contained in a tankcar.

Current practices require labeling of tanks and tankcars for the type of fuel stored or transported, and for the recipient of fuel (normally the storage tank operator) to test the fuel for fuel type prior to unloading a tankcar. The test, at a minimum, consists of taking a sample of the fuel and visually inspecting the sample for color: AVGAS is tinted blue, while jet fuel is clear or has a slight yellow tint. However, it has been the inventor's experience that in many instances, the fuel recipient fails to preform the test, or mistakenly interprets the test results. Consequently, fuel types can be mixed, either in loading of the tankcar, or loading of the onsite storage tank. At a minimum, if the error is discovered prior to use of the fuel, the tank or tankcar must be purged and cleaned, and contaminated product must be properly disposed, both time consuming and expensive procedures.

SUMMARY OF THE INVENTION

The invention disclosed is a device for distinguishing between two liquids based upon a difference in specific gravity. In particular, the device is suitable for distinguishing jet fuel from AVGAS prior to transferring liquids into a storage vessel. The device has a container with two float switches placed therein. The first float switch is normally open and is floatable in either liquid, while the second float switch is floatable in the liquid with the greater specific gravity; the second float switch can be normally open or normally closed based upon the device configuration. The second float switch is wired in series with the first float switch, and hence, is activated when first float switch closes. When a sample of liquid is placed in the container, the position of the two float switches allows an operator to distinguish one liquid from another. The device is intended to be attached to a liquid storage vessel for a liquid of known specific gravity. Consequently, the second float switch be adapted to signal the presence of a liquid in the container of compatible specific gravity or incompatible specific gravity. The second float switch signal can thus be used to operate devices to assist fluid flow into the storage tank (for compatible liquids) or to hinder fluid flow into a storage tank (for incompatible liquids).

Various tamper resistant measures can be incorporated in the device to help insure that the device operates as intended. The device can incorporate a cover which obstructs the tank fill pipe unless the cover is removed, preventing the connection of a hose between the tank fill pipe and tankcar, thus preventing fluid from entering the tank. The device can have a cover switch which, when the cover is opened, sends a signal to a device which prevents the transfer of liquid into a storage tank. Structural features of the device prevents an operator from interfering with the proper operation of the float switches or the cover switch.

OBJECTS OF INVENTION

Accordingly, it is an object of the present invention to provide a device to distinguish liquids based upon differences in specific gravity.

It is another object of the present invention to provide a device to distinguish between aviation fuels, i.e. jet fuel and AVGAS, prior to transferring an aviation fuel into a storage vessel containing a known aviation fuel type.

It is another object of the invention to provide a tamper resistant device to distinguish between aviation fuels.

DETAILED DESCRIPTION OF THE INVENTION

Figure 1:
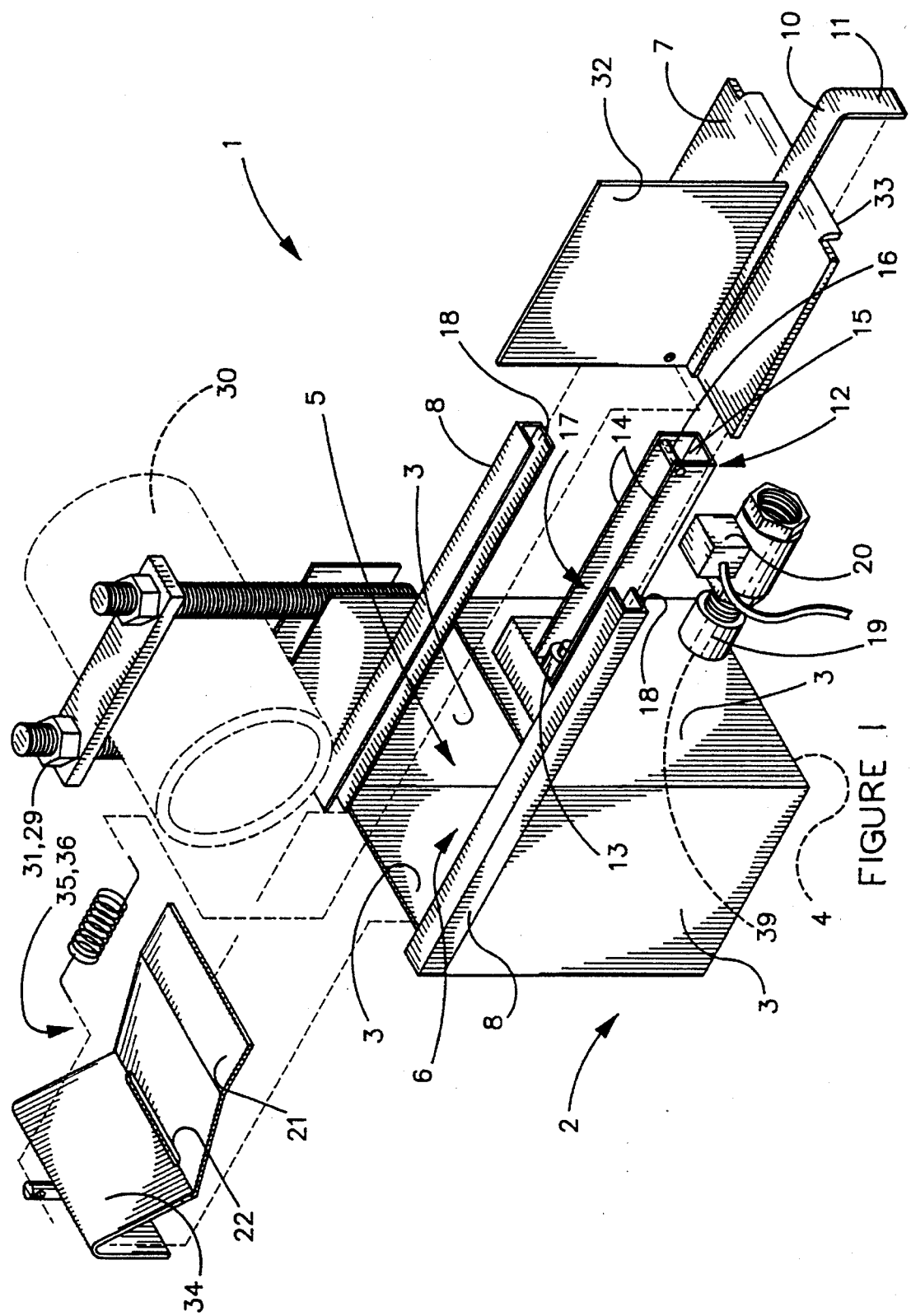
FIG. 1 is an exploded prospective view of an embodiment of the invention.

Turning to the drawings, FIG. 1 shows an exploded prospective view of the device 1. Device 1 has a container 2 having sidewalls 3, a base 4 and an open end 5 defining an interior 6 therein. Projecting horizontally outward from the sidewalls 3 is a U-shaped guide 12 with sides 14 and bottom 15, the sides 14 and bottom 15 defining a guidepath 17. Open end 5 has two channels 8 attached thereon and extending horizontally outward therefrom substantially parallel to U-shaped guide 12. Cover 7 is slidable within channels 8. Preferably, channels 8 extend sufficiently to allow cover 7 to fully open yet remain partially engaged in the channels 8.

Figure 3:
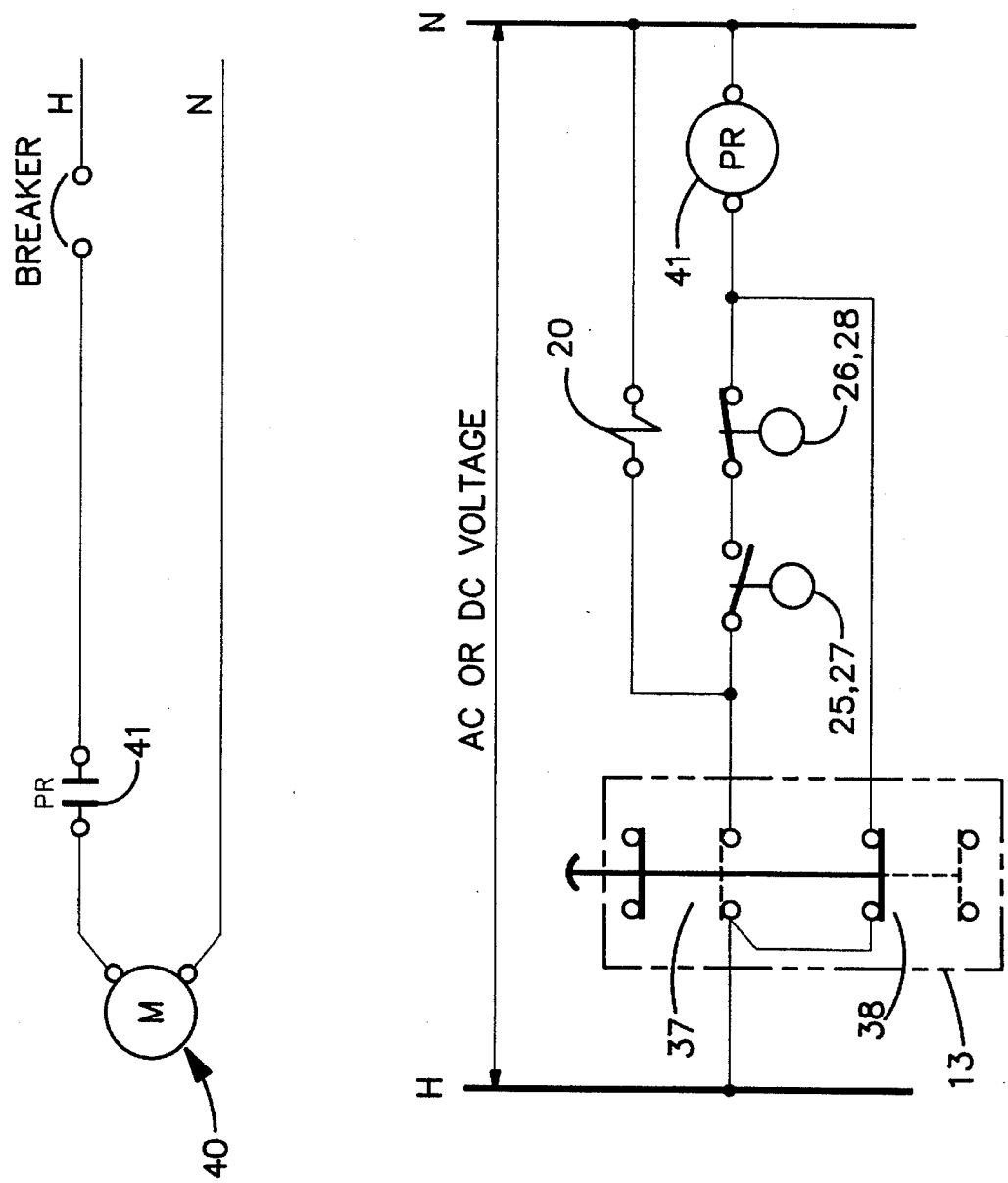
FIG. 3 is a wiring schematic of an embodiment of the invention.

The cover 7 has a tailpiece 10 projecting outwardly and parallel to U-shaped guide 12 and having a switch end 11. Switchend 11 is shaped to be slidable in guidepath 17 and engagable with switch means 13. Switch means 13 is positioned adjacent to sidewall 3 in U-shaped guide 12 for contacting switchend 11 of tailpiece 10 of cover 7 when cover 7 closes open end 5. Switch means 13 detects the status of cover 7 as open or closed. Preferably, switch means 13 is multi-function pushbutton contact or magnetic switch. When cover 7 closes, switchend 11 of tailpiece 10 engages and opens first switch contact 37 of switch means 13; when cover 7 opens, switchend 11 of tailpiece 10 disengages from first switch contact 37 of switch means 13, thereby closing first switch contact 37. In one embodiment, when cover 7 is open, first switch contact 37 of switch means 13 generates a switch signal when closed. As shown in FIG. 3, switch signal can be used to control a relay 41 which can perform a variety of tasks, such as to initially prevent flow of liquid into tank fill line 30, by signaling stop mean 40, such as a valve (not shown) located in fill tank line 30 to close fill tank line 30, or to signal a pump (not shown) to cease pumping liquid into tank fill line 30 or similar activity to prevent liquid from entering a tank. Switch signal can later be changed to enable pump or open valve to allow fluid to flow into storage tank if device detects the appropriate fluid. When stop means 40 is incorporated with device 1, fluid cannot enter tank fill line 30 until a sample of fluid has been inserted into device 1 and tested for suitability thereby providing an additional measure of safety.

As shown in FIG. 3, switch means 13 may have a second switch contact 38. If the device 1 is configured to signal a pump to cease pumping when cover 7 is opened, second switch contact 38 is normally open and can be wired to signal pump to enable pump when cover 7 is closed. In this fashion, the pump used to fill tank may also be used to remove fluid from tank. Thus, when the cover 7 is closed, second switch contact 38 closes, enabling pump to be operated. Note in this configuration, pump may be operated when cover 7 is closed, but is initially disabled when cover 7 is open. FIG. 3 indicates a separate power source for device 1; it is also possible to supply power to device 1 by tapping the pump power supply with suitable conditioning of that power (i.e. steping down the voltage).

To prevent tampering with switch means 13, sides 14 of U-shaped guide 12 are sized to slidably contact cover 7 as cover 7 slides in channels 8, thereby effectively covering U-shaped guide 12 and preventing an operator from inserting a finger or other device in the guide to operate switch means 13. In another embodiment, cover 7 can be bent downward 90 degrees adjacent to the tailpiece 10 to form a lip 33 for slidably contacting the sides 14 of U-shaped guide 12. To prevent removal of cover 7 from device 1, U-shaped guide 12 may have a blocking means for preventing the cover 7 from sliding off the device 1. Such a blocking means could include a projection into the U-shaped guide 12, such as a bolt or rivet 16, which extends from one side 14 into the guidepath 17 of the U-shaped guide 14 to block the movement of tailpiece 10 beyond the position of blocking means. Alternatively, blocking means could be a plate to close the end U-shaped guide 12 distant from container. The blocking means should be positioned on sides 14 to allow cover 7 to fully open. Alternatively, channels 8 could have closable ends 18 to prevent cover 7 from sliding off channels 8.

An opening through the sidewalls 3 near base 4 forms a drain 39 for voiding fluids placed in interior 6. Positioned in drain 39 is a conventional drain valve 19. Preferably, device 1 incorporates solenoid 20, solenoid 20 is responsive to switch means 13 to open drain valve 19 when cover 7 is closed, and to close drain valve 19 when cover 7 is open. In this fashion, interior 6 will retain fluids only when cover 7 is open; consequently, device 1 will not retain rainwater in interior 6 when cover is closed.

Fill plate 21 is positioned between open end 5 and cover 7 and sufficiently closes open end 5 so that an operator may not access the interior 6 of container 2. Fill plate 21 has a fill opening 22 therethrough for allowing fluids to enter interior. Preferably, fill plate 21 is adapted to allow an operator to determine the fluid level in interior 8. In the embodiment shown in FIG. 1, fill plate 21 has a portion 34 V-shaped in cross-section which projects into the interior of container 2. However, any shape which projects into the interior 6 would be suitable. As shown in FIG. 1, fill opening 22 is a slot located on the portion 34 of fill plate 21 extending into container 2 a distance which corresponds to the desired fluid level in container 2. Thus, fluid can be poured into the interior 6 of container 2 until fluid level rises in container 2 sufficient to immerse fill opening 22 indicating that the desired fluid level has been reached.

Figure 2:
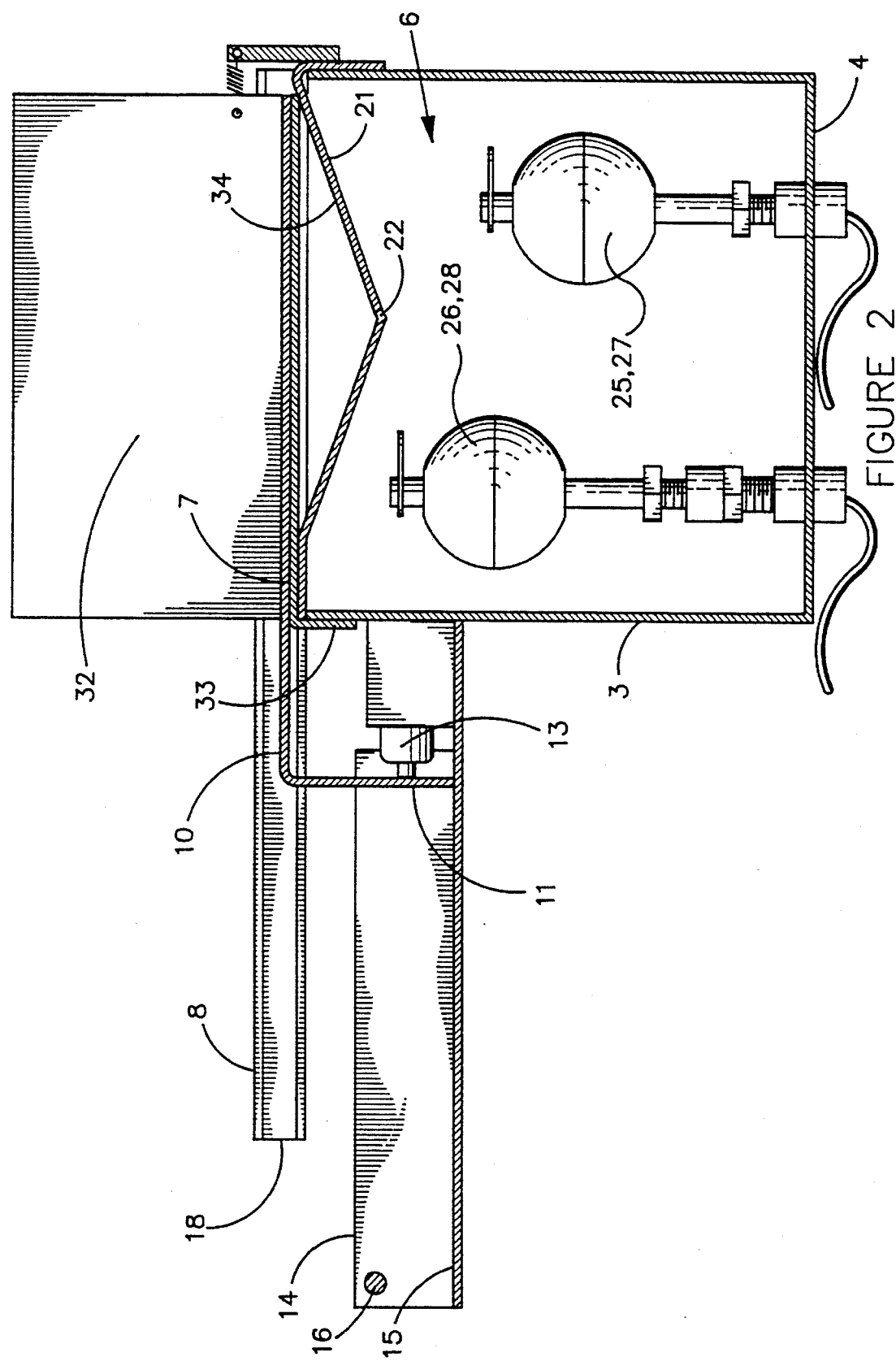
FIG. 2 is a cross sectional view of the embodiment of the invention depicted in FIG. 1.

As shown in FIG. 2, positioned in the interior 6 is first signal means 25 and second signal means 26. First signal means 25, when activated, generates a first signal when container contains a minimum quantity of liquid with a specific gravity greater than or equal to a first selected specific gravity, A. First signal means 25 is activated by switch means 13 upon opening of cover 7.

Second signal means 26, when activated, responds to the presence or absence of a minimum quantity of liquid in container 2 with a specific gravity greater than or equal to B, where A<B. Generally, second signal means 26 will be activated by the first signal from first signal means 25. Second signal means 26 can be designed to generate second signal when a fluid of specific gravity C is present and where A<C≤B. Alternatively, second signal means can be designed to generate second signal when A<B≤C. Additionally, device 1 can be set to positively detect fluid, that is, to respond when a fluid with the desired specific gravity is present, or to negatively detect fluid, that is, to respond when the desired fluid is absent.

In the embodiment shown in FIG. 2, first signal means 25 is a first float switch 27, normally open, which is activated when switch means 13 indicates cover 7 is open. Second signal means 26 is a second float switch 28, wired in series with first float switch 27. Consequently, the presence of a liquid with specific gravity greater than or equal to A closes first float switch 27 sending power to second float switch 28 (generation of first signal).

In the embodiment shown in figure 2, second float switch 28 can either be normally open or normally closed. If device 1 is set to positively detect liquids with specific gravity C, where A≤C<B, then second float switch 28 will be normally opened. If device 1 is set to positively detect liquids with specific gravity C, where B<C, then second float switch 28 will be normally closed. Alternatively, if device 1 is set to negatively detect fluids with specific gravity C, where A<C≤B, then second float switch 28 will be normally closed; if device 1 is set to negatively detect liquids with specific gravity C, where B≤C, then second float switch 28 will be normally opened.

For instance, suppose device 1 is to detect AVGAS (American Petroleum Institute "API" relative density range of 0.66 to 0.76) and to sound an alarm wired in series with first and second float switches 27, 28 (or operated a relay to sound an alarm) if jet fuel (API relative density range of 0.77 to 0.86) is present (negative detection). In this instance, first float switch 27 is sized to float when the liquid in interior 6 equals or exceed the specific gravity of AVGAS (e.g. 0.66), while second float switch 28 is sized to float when the specific gravity equals or exceeds that of jet fuel (e.g. 0.76). First float switch 27 is normally open, and second float switch 28 is normally open. In the presence of AVGAS, first float switch 27 floats, closing, sending power to second float switch 28. Second float switch 28 does not float and remains open, preventing power from being sent to an alarm (or to relay). If, however, jet fuel is present, first float switch 27 floats, closing, sending power to second float switch 28, and second float switch 28 floats, closes and sends power to alarm (or to relay).

If, however, device 1 is to detect AVGAS and operate a solenoid to open a normally closed valve (or operate a relay to open such a valve) to tank fill line 30 if AVGAS is present (positive detection), then first float switch 27 is sized to float in a liquid with a specific gravity that equals or exceeds that of AVGAS and is normally open, second float switch 28 is sized to float in a liquid with specific gravity that equals or exceeds that of jet fuel and is normally closed. In the presence of AVGAS, first float switch 27 floats, sending power to second float switch 28, second float switch 28 does not float and hence power is sent to solenoid to open valve (or to relay to operate valve) allowing jet fuel into tank. In the presence of jet fuel, first float switch 27 floats, sending power to second float switch 28, second float switch 28 floats, opening the circuit, keeping solenoid from opening valve.

As shown in FIG. 1, device 1 may have an attachment means 29 for attaching device 1 to the tank fill line 30. Attachment means 29 can be a clamp means, a weld, or any other means to secure device 1 to fill line 30. In the embodiment shown in FIG. 1, attachment means 29 is a clamp 31. Also shown in FIG. 1 is flange 32. Flange 32 is mounted vertically on cover 7 to block tank fill line 30 when cover 7 is closed, thus preventing an operator from bypassing use of device 1. Positioned between fill plate 21 and flange 32 of cover 7 is resilient means 35. Resilient means 35 is for maintaining cover 7 in the closed position when device 1 is not in use. As shown in FIG. 1, resilient means 35 can be a spring 36. Resilient means 35 and flange 32 are additional safety measures insuring that cover 7 remains closed when not in use thus preventing an operator from attaching a hose to fill line 30 without activating device 1 by opening cover 7.

I claim:

1. A device to verify the identity of a selected fluid before permitting said fluid to be introduced into a storage vessel containing a liquid of known specific gravity, comprising:
   (a) a container constructed from connecting walls to form a chamber, one of said walls having an opening through which said selected fluid may be introduced;
   (b) a first means positioned in said container for generating a first signal when contacted by a fluid having a specific gravity greater than a first predetermined amount;
   (c) a second means positioned in said container for generating a second signal in the presence of a fluid having a specific gravity greater than a second predetermined amount, where said first predetermined amount is less than said second predetermined amount, said second means being responsive to said first signal;
   (d) a lid, said lid closing said opening and removably connected to said container, said lid of said container further having a flange mounted perpendicularly thereon, said flange obstructing a fill line only when said lid closes said opening; and
   (e) a means for generating a third signal upon removal of said lid from said opening, said means for generating a first signal being responsive to said third signal.

2. A device according to claim 1 further having a verifying means for receiving said second signal, said verifying means further operatively responding to said second signal.

3. A device according to claim 2 wherein said verifying means is an alarm.

4. A device according to claim 2 wherein said verifying means is valve solenoid.

5. A device according to claim 2 wherein said verifying means is a pump.

6. A device according to claim 1 wherein said first means is a first float switch, said second means is a second float switch, said second float switch responsive to said first float switch.

7. A device according to claim 1 wherein said means for generating a third signal is a multi-function contact switch.

8. A device according to claim 7 further having a stop means to prevent flow of liquid into said storage vessel, said stop means responsive to said third signal.

9. A device according to claim 1 wherein said first predetermined amount is in the range of American Petroleum Institute (API) relative density 0.66 to 0.76.

10. A device according to claim 9 wherein said second predetermined amount is in the range of American Petroleum Institute (API) relative density 0.77 to 0.86.

* * * * *